United States Patent [19]

Verkade

[11] Patent Number: 5,051,533
[45] Date of Patent: Sep. 24, 1991

[54] PROPHOSPHATRANE COMPOUNDS AS PROTON ABSTRACTING REAGENTS

[75] Inventor: John G. Verkade, Ames, Iowa

[73] Assignee: Iowa State University Research Foundation, Inc., Ames, Iowa

[21] Appl. No.: 510,620

[22] Filed: Apr. 18, 1990

[51] Int. Cl.$^5$ .................................. C07F 9/6524
[52] U.S. Cl. ............................................. 564/13
[58] Field of Search ................................. 564/13

[56] References Cited

U.S. PATENT DOCUMENTS

| | | | |
|---|---|---|---|
| 3,987,128 | 10/1976 | Richman | 564/13 |
| 3,996,276 | 12/1976 | Atkins | 564/13 |
| 4,038,312 | 7/1977 | Atkins | 564/13 |

OTHER PUBLICATIONS

Abstract of J. Am. Chem. Soc. (1989), vol. 11, p. 3478.

Primary Examiner—Mary C. Lee
Assistant Examiner—Michael G. Ambrose
Attorney, Agent, or Firm—Zarley, McKee, Thomte, Voorhees & Sease

[57] ABSTRACT

Prophosphatrane compounds of the formula

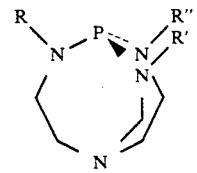

are disclosed. These compounds are strong Lewis bases and are useful as proton abstracting reagents.

11 Claims, No Drawings

PROPHOSPHATRANE COMPOUNDS AS PROTON ABSTRACTING REAGENTS

BACKGROUND OF THE INVENTION

1. Field of the Invention

This invention relates to certain bicyclic phosphorus compounds known as prophosphatranes. More specifically it relates to the prophosphatrane compounds, their use as deprotonating agents and to methods of synthesis of these compounds.

2. Description of the State of the Prior Art

Chemists are often in need of strong proton (H+) abstracting reagents. For that purpose there are commercially available reagents which are known to be useful to abstract a proton from a wide variety of organic, organometallic, or inorganic substrates. To be an ideal proton abstractor, or in other words a very strong Lewis base, it is best if the reagent has the capability of abstracting protons from molecules reluctant to release protons and of holding the abstracted proton tightly. It is also preferred, for ease of processing in complex organic synthesis, that once the proton abstractor has done its job, that it not induce unwanted side reactions and that it be easily separable as a stable product from the remaining portion of the reactants by adding or generating a halide such as chloride as shown in Reactions 1 and 2, respectively.

(1)

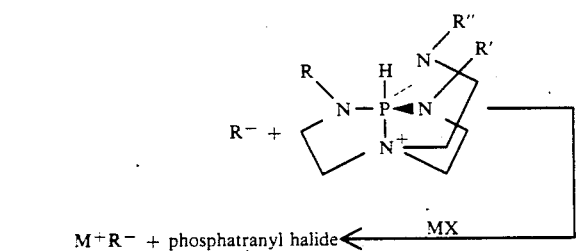

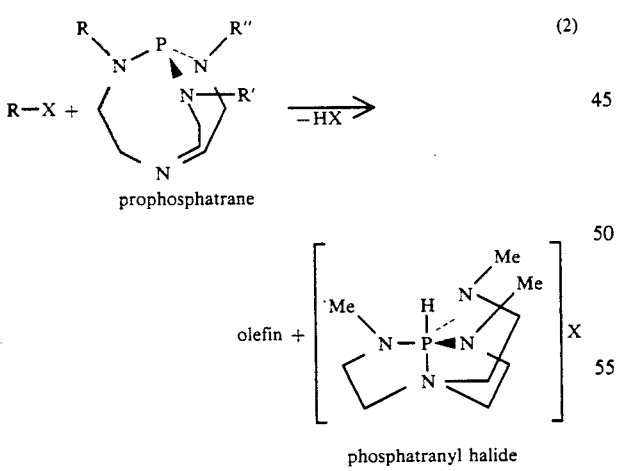

(2)

In Reaction 1, MX could be lithium chloride, for example. There is, therefore, a continuing need for the development of new proton abstracting reagents to take the place of less effective proton abstractors currently on the market.

Proton abstractors such as those commercially available from firms such as Aldrich Chemical Company, are commonly utilized to form R⁻ ions from RH substrates. An example of such a compound available from Aldrich Chemical Company is 1,8-(bisdimethylamino)-naphthalene, sold under the trademark PROTON SPONGE. The compounds of the present invention are considerably stronger proton abstracting agents than PROTON SPONGE i.e. they remove protons from substrates that PROTON SPONGE leaves intact.

SUMMARY OF THE INVENTION

In accordance with this invention prophosphatrane compounds have been discovered which are of the formula:

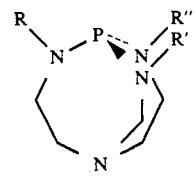

wherein R, R' and R" are like or different and are selected from the group consisting of hydrogen and C₁ to C₈ alkyl. The compounds are powerful Lewis bases useful in a variety of organic syntheses, including the synthesis of drugs and pharmaceuticals, as well as certain other more common industrial processes wherein strong Lewis bases are used in at least one step in the process.

DETAILED DESCRIPTION OF THE INVENTION

The present invention relates to preparation of very strong proton abstractors. Technically speaking, they are very strong Lewis bases. The compounds of the present invention are better than any known commercially available proton abstracting reagents, in that they have the advantages of being easily prepared, are highly effective in performance, and under appropriate conditions produce insoluble stable products after abstracting protons. Because of the insolubility of their halide salts in many organic solvents commonly used in synthesis, these products can easily be removed from the reaction system without difficulty. Moreover, compounds of the present invention have the advantage over stronger proton abstractors such as tertiary butoxide salts that, unlike the latter, they are not nucleophilic and therefore are not prone to initiate unwanted side reactions. They are therefore useful for proton abstraction of a wide variety of compounds that are organic, inorganic, or organometallic in nature.

The compounds of the present invention are prophosphatrane compounds of the formula:

wherein R, R' and R" are alike or different, and each are selected from the group consisting of hydrogen and C₁ to C₈ alkyl. It is preferred that R, R' and R" are selected from the group consisting of hydrogen and C₁ to C₄, and most preferably hydrogen and methyl. Generally, the lower the number of carbons for R, R' and R", the less soluble the reaction product after abstracting the proton.

Examples of suitable moieties for R, R' and R" are hydrogen, methyl, ethyl, propyl, isopropyl, butyl, isobutyl, tertiary butyl, pentyl, hexyl, octyl, and aryl.

As illustrated in the examples, the compounds of the present invention can be made by a straightforward pair of reactions. In the first step a trialkyl tris-beta-aminoethylamine (trialkyl-TREN) is reacted, preferably with an equimolar amount of bis-dimethylaminochlorophosphine to provide the phosphatranyl chloride in Scheme 1.

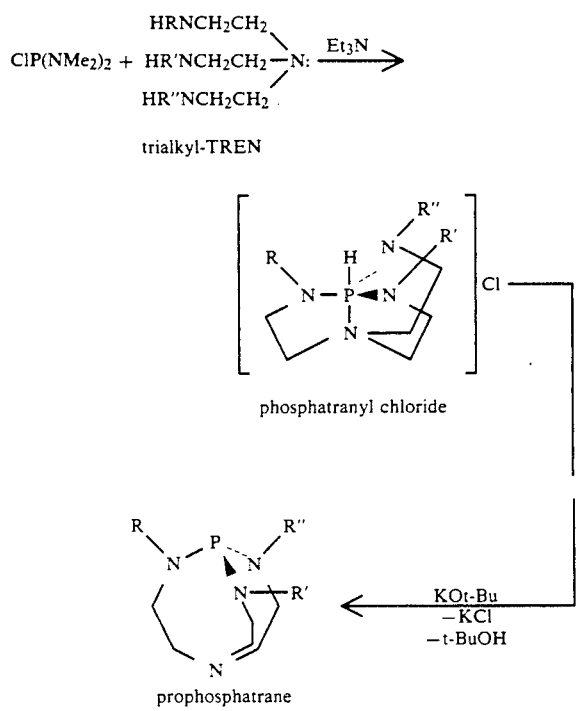

Preferably this reaction is conducted in the presence ©f an organic solvent, with no criticality of temperature. Room temperature works fine. Suitable solvents include chlorinated hydrocarbons, aromatic hydrocarbons, and ethers. A highly preferred solvent is methylene chloride. This reaction proceeds in an essentially stoichiometric fashion. The starting (TREN) compound is commercially available from W. R. Grace and Company. In the second step of the synthesis, phosphatranyl chloride is converted to the prophosphatrane in the presence of an organic base such as potassium tertiary butoxide in acetonitrile solvent at room temperature.

As illustrated in the examples below, the compounds of the present invention, once prepared, are highly useful in a variety of organic syntheses to remove a proton from another reactant, making it reactive for subsequent use in organic synthesis. The phosphatranyl cation found in reactions such as 1 and 2 from the compounds of the present invention are easily removed since they are highly insoluble with anions such as chloride. Alternately, the deprotonated reactant can be further processed in the presence of the phosphatranyl cation since the latter is quite inert to further reaction. In performing the deprotonating reaction of the present invention, a stoichiometric or excess amount of the deprotonating agent should be utilized. If less is utilized the amount of deprotonation is less than it should be, and correspondingly the amount of desired deprotonated reaction product is decreased.

The following example is offered to illustrate but not limit the process of the present invention.

EXAMPLE

The prophosphatrane wherein R, R' and R" equal methyl is prepared as the chloride by adding a solution of $(HMeNCH_2CH_2)_3N$ (1.67 g, 11.4 mmol) in $CH_2Cl_2$ (20 mL), over a period of 5 min to a stirred solution of $ClP(NMe_2)_2$ (1.76 g. 11.4 mmol) and $Et_3N$ (1.5 g, 15 mmol) in $CH_2Cl_2$ (30 mL). Stirring at room temperature for 1 h followed by removal of the solvent and $Et_3N$ afforded the phosphatranyl chloride in essentially quantitative yield. The salt was recrystallized from hexane/chloroform at $-20°$ C. to give an 82% yield of the product as a colorless crystalline solid. Treatment of the compound $(Cl^-)$ with $AgBF_4$ in $CH_2Cl_2$ gave the $BF_4^-$ salt in quantitative yield. X-ray crystallography of the $BF_4^-$ salt confirmed the presence of the phosphatranyl cation phosphatrane wherein R, R' and R" are methyl. The product was converted to the corresponding prophosphatrane by adding 0.87 g (3.4 mmol) of the salt dissolved in 10 mL of acetonitrile to a suspension of potassium tertiary butoxide (0.41 g, 3.7 mmol) in acetonitrile (20 mL). After stirring the reaction mixture for 30 minutes at room temperature, the solvent was removed under vacuum and the residue extracted with $2\times30$ mL of hexanes. The white residue was purified by vacuum sublimation (60° C./0.01 mm Hg) to give the prophosphatrane (R=R'=R"-Me) in 82% yield.

The first indication of the remarkable stability of this compound became evident in step one of Scheme 1. The presence of triethylamine was intended to remove HCl, thereby leading directly to the synthesis of the prophosphatrane in Scheme 1. Instead, the phosphatranyl chloride was isolated.

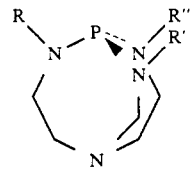

Furthermore, efforts to remove the proton of this chloride with DBU in DMSO, n-BuLi in THF, $CaH_2$ in $CH_2Cl_2$, or KOH in refluxing toluene led only to the recovery of the phosphatranyl chloride. Slowly heating the phosphatranyl chloride with a large excess of anhydrous NaOH to 200° C. under vacuum over a period of several hours also gave no indication of reaction.

Indeed, the trimethyl prophosphatrane compound of the present invention deprotonates PhOH ($pK_a=10$), $(CN)_2CH_2$ ($pK_a=11$), protonated PROTON SPONGE (1,8-(bisdimethylamino)-naphthalene-HCl, $pK_1=12.3$), $(EtOOC)_2CH_2$ ($pK_a=13$), and $H_2O$ ($pK_a32$ 12.3). This demonstrates that the proton abstracting capability of the present compound is much stronger than the strongest commercially available products, proton sponge and DBU.

It therefore can be seen that the invention accomplishes at least all of its stated objectives.

What is claimed is:

1. A prophosphatrane compound of the formula:

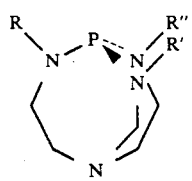

wherein R, R' and R" are selected from the group of hydrogen, and $C_1$ to $C_8$ alkyl.

2. A prophosphatrane compound of claim 1 wherein each of R, R' and R" are selected from the group consisting of hydrogen and $C_1$ to $C_4$.

3. A prophosphatrane compound of claim 1 wherein each of R, R' and R" are selected from the group consisting of hydrogen and methyl.

4. A prophosphatrane compound of claim 3 wherein each of R, R' and R" are methyl.

5. A prophosphatrane compound of claim 3 wherein each of R, R' and R" are hydrogen.

6. A method of preparing a prophosphatrane compound of the formula:

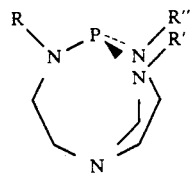

wherein R, R' and R" are selected from the group consisting of hydrogen, and $C_1$ to $C_8$ alkyl, said method comprising:
(a) reacting trialkyl tris-beta-amino-ethylamine with bis dimethylaminochlorophosphine; and thereafter
(b) converting the reaction product of step (a) to a prophosphatrane by reacting the product of step (a) with an organic base in the presence of a solvent.

7. The method of claim 6 wherein the reaction is conducted in the presence of a solvent selected from the group consisting of chlorinated hydrocarbons, aromatic hydrocarbons and ethers.

8. The method of claim 6 wherein the solvent is a chlorinated hydrocarbon.

9. The method of claim 8 wherein the solvent is methylene chloride.

10. The method of claim 6 wherein the organic base is a strong organic base.

11. The method of claim 10 wherein the strong organic base is potassium tertiary butoxide.

* * * * *